United States Patent [19]

Krapcho

[11] 4,214,081
[45] Jul. 22, 1980

[54] IMINO CONTAINING MORPHOLINE COMPOUNDS

[75] Inventor: John Krapcho, Somerset, N.J.

[73] Assignee: E. R. Squibb & Sons, Inc., Princeton, N.J.

[21] Appl. No.: 973,197

[22] Filed: Dec. 26, 1978

Related U.S. Application Data

[62] Division of Ser. No. 916,979, Jun. 19, 1978, Pat. No. 4,156,079.

[51] Int. Cl.² .................................... C07D 295/12
[52] U.S. Cl. .................................... 542/424; 542/423; 544/162; 544/165; 544/167
[58] Field of Search ............. 544/162, 165, 167; 542/424, 423

[56] References Cited
U.S. PATENT DOCUMENTS

| | | | |
|---|---|---|---|
| 2,774,766 | 12/1956 | Goldberg et al. | 260/294.7 |
| 4,064,125 | 12/1977 | Krapcho | 424/254 |

OTHER PUBLICATIONS

Millonig et al., "Chem. Abstracts" vol. 81 (1974), No. 163,333x.
Geller et al., "Chem. Abstracts" vol. 83 (1975), No. 141,972u.

*Primary Examiner*—Henry R. Jiles
*Assistant Examiner*—R. W. Ramsuer
*Attorney, Agent, or Firm*—Lawrence S. Levinson; Donald J. Barrack

[57] ABSTRACT

Compounds having the formula

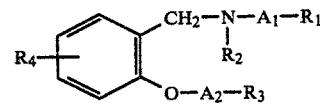

or a pharmaceutically acceptable salt thereof, wherein $R_1$ is alkyl, cycloalkyl or aryl; $R_2$ is acyl or sulfonyl; $R_3$ is alkylamino, dialkylamino or a nitrogen containing heterocyclic group; $R_4$ is alkoxy; $A_1$ is a saturated bond or an alkylene group having 1 to 4 carbon atoms; and $A_2$ is an alkylene group having 2 to 5 carbon atoms; have antiinflammatory activity.

4 Claims, No Drawings

IMINO CONTAINING MORPHOLINE COMPOUNDS

This is a division, of application Ser. No. 916,979, filed June 19, 1978, now U.S. Pat. No. 4,156,079.

BACKGROUND OF THE INVENTION

U.S. Pat. No. 4,064,125, issued Dec. 20, 1977 to John Krapcho, discloses antiinflammatory compounds (and salts thereof) having the formula

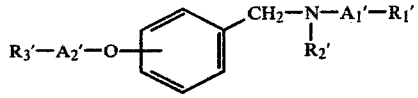

wherein $R_1'$ is alkyl, cycloalkyl or aryl; $R_2'$ is acyl; $R_3'$ is alkylamino or dialkylamino; $A_1'$ is a saturated bond or an alkylene group having 1 to 4 carbon atoms; and $A_2'$ is an alkylene group having 2 to 5 carbon atoms.

RELATED APPLICATIONS

Several additional United States patent applications have been filed by John Krapcho which disclose compounds that are structurally related to the compounds which make up the invention hereinafter set forth. The applications are continuation-in-part applications of the application that matured into U.S. Pat. No. 4,064,125. The applications are Ser. No. 834,216, filed Sept. 21, 1977; Ser. No. 835,099, filed Sept. 21, 1977; and Ser. No. 835,462, filed Sept. 21, 1977.

These applications disclose antiinflammatory compounds (and salts thereof) having the formula

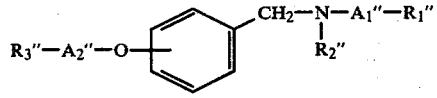

wherein $R_1''$ is alkyl, cycloalkyl or aryl; $R_2''$ is acyl or sulfonyl; $R_3''$ is alkylamino, dialkylamino or a nitrogen containing heterocyclic, $A_1''$ is a saturated bond or an alkylene group having 1 to 4 carbon atoms; and $A_2''$ is an alkylene group having 2 to 5 carbon atoms.

Other antiinflammatory compounds (and salts thereof) that are structurally related to the compounds which make up the invention hereinafter set forth are disclosed in two United States patent applications filed by John Krapcho and Chester F. Turk. The applications are Ser. No. 773,561, filed Mar. 2, 1977 and Ser. No. 897,476, filed Apr. 18, 1978 which is a division of the first application. These applications disclose antiinflammatory compounds (and salts thereof) having the structural formula

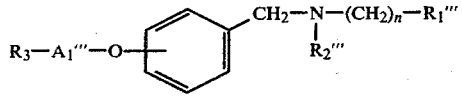

wherein $R_1'''$ is alkoxycarbonyl, amido, or substituted amido; $R_2'''$ is acyl or sulfonyl; and $R_3'''$ is alkylamino, dialkylamino or a nitrogen containing heterocyclic group; $A_1'''$ is an alkylene group having 2 to 5 carbon atoms; and n is 1, 2 or 3.

BRIEF DESCRIPTION OF THE INVENTION

Compound having the formula

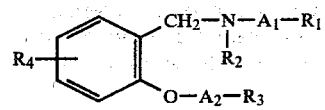

and the pharmaceutically acceptable salts thereof, have useful antiinflammatory activity. In formula I, and throughout the specification, the symbols are as defined below.

$R_1$ is alkyl, cycloalkyl or aryl;
$R_2$ is

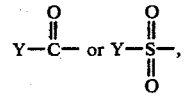

wherein
Y is alkyl, cycloalkyl, aryl, arylalkyl, styryl, or styryl wherein the phenyl group is substituted with a halogen, alkyl, alkoxy, trifluoromethyl, nitro or amino group;
$R_3$ is alkylamino, dialkylamino or a nitrogen containing heterocyclic group selected from 1-pyrrolidinyl, 1-piperidinyl, 4-morpholinyl, 1-piperazinyl, and 4-alkyl-1-piperazinyl;
$R_4$ is alkoxy (methoxy is preferred);
$A_1$ is a saturated bond or an alkylene group having 1 to 4 carbon atoms; and
$A_2$ is an alkylene group having 2 to 5 carbon atoms.

The terms "alkyl" and "alkoxy", as used throughout the specification, whether by themselves or as part of larger groups, refer to groups having 1 to 6 carbon atoms.

The term "aryl," as used throughout the specification, whether by itself or as part of a larger group, refers to phenyl or phenyl substituted with a halogen, alkyl, alkoxy, trifluoromethyl, nitro, or amino group.

The term "halogen," as used throughout the specification, refers to fluorine, chlorine, bromine and iodine; chlorine and bromine are preferred.

The term "cycloalkyl," as used throughout the specification, refers to cycloalkyl groups having 3 to 7 carbon atoms.

The term "alkylene," as used throughout the specification, refers to a straight or branched chain, divalent, saturated hydrocarbon group.

DETAILED DESCRIPTION OF THE INVENTION

The compounds of this invention can be prepared using as starting materials a 2-hydroxybenzaldehyde having the formula

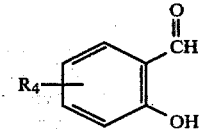

and a compound having the formula

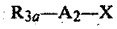

III wherein X is a halogen atom or other leaving group and $R_{3a}$ is alkylbenzylamino, dialkylamino, or a nitrogen containing heterocyclic group.

Reaction of the two starting materials (formulas II and III) and a strong base, e.g., sodium hydride, sodium hydroxide, or the like, yields an intermediate having the formula

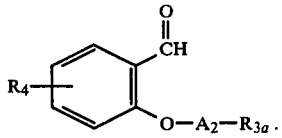

IV

The reaction can be run in an organic solvent, e.g., benzene, xylene, toluene, or the like; reaction conditions are not critical, but the reaction will preferably be run at an elevated temperature. In a preferred embodiment of this invention, the 2-hydroxybenzaldehyde of formula II is first treated with a strong base in a polar organic solvent, and subsequently reacted with a compound of formula III in an aromatic hydrocarbon solvent.

An intermediate of formula IV can be reacted with a primary amine having the formula

V to yield the corresponding Schiff base having the formula

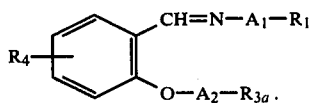

VI

The reaction can be run in an organic solvent, e.g., an aromatic hydrocarbon, and will preferably be run at the reflux temperature of the solvent.

Reduction of a compound of formula VI, using chemical or catalytic means, yields the corresponding intermediate having the formula

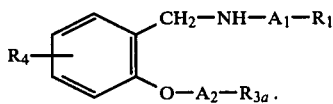

VII

The reaction can be run using gaseous hydrogen in the presence of a catalyst such as Raney nickel or palladium. Preferably, the reaction will be run using a chemical reducing agent such as sodium borohydride.

The Schiff bases of formula VI and the compounds of formula VII are novel compounds useful in the preparation of the antiinflammatory compounds of formula I; as such, they constitute a part of this invention.

The products of formula I, wherein $R_3$ is dialkylamino or a nitrogen containing heterocyclic group can be prepared by reacting the corresponding compound of formula VII with the appropriate acid or sulfonyl halide, preferably the acid or sulfonyl chloride ($R_2$—Cl) or, when $R_2$ is acyl, an acid anhydride (($YCO)_2O$) can also be used. The reaction can be run in an organic solvent, e.g., a halogenated hydrocarbon such as chloroform. The products of formula I, wherein $R_3$ is alkylamino can be prepared by first reacting the corresponding compound of formula VII wherein $R_{3a}$ is alkylbenzylamino with an acid or sulfonyl halide or acid anhydride, as described above, to yield an intermediate having the formula

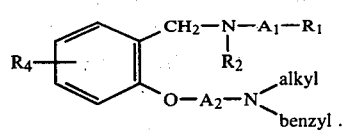

VIII

Debenzylation of a compound of formula VIII using the well-known catalytic hydrogenation procedure yields the corresponding product of formula I.

Those products of formula I wherein the $R_1$ or $R_2$ group contains an amino substituent are preferably prepared by reduction of the corresponding nitro compound.

The pharmaceutically acceptable salts of the compounds of formula I are readily prepared using procedures well known in the art. Acid addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

The following examples are specific embodiments of this invention.

EXAMPLE 1

4-Chloro-N-[[5-methoxy-2-[3-(4-morpholinyl)-propoxy]phenyl]methyl]-N-(2-phenylethyl)-benzamide, hydrochloride salt (1:1)

A.
5-Methoxy-2-[3-(4-morpholinyl)-propoxy]benzaldehyde

A stirred solution of 25 g of 2-hydroxy-5-methoxybenzaldehyde in 125 ml. of dimethylformamide is treated portionwise with 8.2 g of 50% sodium hydride (oil dispersion). The temperature is kept below 35° C. by means of an ice-water bath. When the addition is complete, the mixture is warmed to 70° C. and cooled to 25° C. This is followed by the addition of a solution of 36 g. of N-(3-chloropropyl)morpholine in 65 ml. of toluene. The mixture is stirred and heated at 100°–105° C. for 4 hours, cooled, poured into 300 ml. of ice-water and extracted with three 150 ml. portions of ether. The combined ether layers are then extracted with 40 ml. of cold 1:1 hydrochloric acid, followed by 20 ml of water. The aqueous phases are combined, layered over with 150 ml of ether, stirred and basified with 40 g. of potassium carbonate. The layers are separated and the aqueous phase is extracted with three 100 ml portions of ether. The combined ether layers are dried over magnesium sulfate. The solvent is removed on a rotary evaporator and the residue is distilled to give 34 g. of the title compound, boiling point 180°–185° C. at 0.1–0.2 mm of Hg.

B.
4-[3-[4-Methoxy-2-[[(2-phenylethyl)-imino]methyl]-phenoxy]propyl]morpholine 5-Methoxy-2-[3-(4-morpholinyl)propoxy]-benzaldehyde (33.4 g) and 14.5 g of phenethylamine are refluxed in 120 ml of toluene for about 1 hour. After cooling to about 50° C., the solvent is removed using a rotary evaporator and the oily residue is distilled to give 42.1 g of the title compound, boiling point 240°–245° C. at 0.2–0.3 mm of Hg.

C.
4-[3-[4-Methoxy-2-[[(2-phenylethyl)amino]methyl]-phenoxy]propyl]morpholine A stirred solution of 4-[3-[4-methoxy-2-[[(2-phenylethyl)imino]methyl]phenoxy]propyl]-morpholine (41.7 g) in 190 ml of methanol is reduced with 12.4 g of sodium borohydride (added portionwise). A cold water bath is used to maintain the temperature of the reaction mixture at 35° C. After 3 hours, the solvent is treated with water and the product is extracted two times with ether. The ether fractions are combined, treated with water, dried and concentrated to give 33.3 g of the title compound, boiling point 249°–254° C. at 0.3–0.4 mm of Hg.

D.
4-Chloro-N-[[5-methoxy-2-[3-(4-morpholinyl)propoxy]phenyl]methyl]-N-(2-phenylethyl)benzamide, hydrochloride A solution of 16.0 g. of 4-[3-[4-methoxy-2-[[(2-phenylethyl)amino]methyl]phenoxy]propyl]-morpholine in 50 ml. of chloroform is added dropwise (at 10°–15° C.) to a stirred solution of 7.7 g of p-chlorobenzoyl chloride in 150 ml. of chloroform. After the addition is completed, the solution is stirred at room temperature for 2 hours, heated at reflux for 1 hour, cooled and concentrated to give a glass-like residue. The residue is rubbed under ether, the evaporation repeated and the partly solid residue taken up in 100 ml of acetonitrile. On diluting to 650 ml with ether, seeding and rubbing, the crystalline hydrogen chloride salt separates. After cooling overnight, the product weighs 21.7 g, melting point 137°–139° C. Recrystallization from 50 ml of warm acetonitrile-50 ml of ether, yields 20.3 g of the title compound, melting point 138°–140° C.

EXAMPLE 2
4-Chloro-N-[[2-[3-(dimethylamino)propoxy]-5-methoxyphenyl]methyl]-N-(2-phenylethyl)-benzamide, maleate salt (1:1)

A.
2-[3-(Dimethylamino)propoxy]-5-methoxybenzaldehyde

2-Hydroxy-5-methoxybenzaldehyde (31.2 g) in 170 ml of dimethylformamide is treated first with 10.1 g of 50% sodium hydride, then with 160 ml of a 2 N toluene solution of 3-dimethylaminopropyl chloride, following the procedure described in Example 1A, yielding 34.1 g of the title compound, boiling point 149°–155° C. at 0.2–0.3 mm of Hg.

B.
N-[[2-[3-(Dimethylamino)propoxy]-5-methoxyphenyl]-methylene]benzeneethanamine 2-[3-(Dimethylamino)propoxy]-5-methoxybenzaldehyde (33.5 g) and 17.4 g of phenethylamine are reacted in 140 ml of toluene following the procedure described in Example 1B yielding 39.9 g of the title compound, boiling point 197°–202° C. at 0.2–0.3 mm of Hg.

C.
N-[[2-[3-(Dimethylamino)propoxy]-5-methoxyphenyl]-methyl]benzeneethanamine N-[[2-[3-(Dimethylamino)propoxy]-5-methoxyphenyl]-methylene]benzeneethanamine (39.5 g) is reduced with 13.0 g of sodium borohydride in 200 ml of methanol following the procedure described in Example 1C yielding 29.7 g of the title compound, boiling point 205°–210° C. at 0.4–0.5 mm of Hg.

D.
4-Chloro-N-[[2-[3-(dimethylamino)-propoxy]-5-methoxyphenyl]methyl]-N-(2-phenylethyl)benzamide, maleate salt (1:1)

N-[[2-[3-(Dimethylamino)propoxy]-5-methoxyphenyl]methyl]benzeneethanamine (15 g) and 8.1 g of p-chlorobenzoyl chloride are reacted in 220 ml of chloroform following the procedure described in Example 1D. The syrupy residue from the chloroform evaporation does not crystallize. It is converted to the oily base using potassium carbonate and ether extractions. The oily base (17.3 g) and 4.2 g of maleic acid (the hydrochloride, hydrobromide, methanesulfonate, phosphate, citrate and succinate salts are oils or gums) are dissolved in 60 ml of warm acetonitrile and diluted to 400 ml with ether. On seeding and rubbing, the crystalline maleate salt separates. After 2 days in the cold, there is 21 g of product, melting point 110°–112° C. (sintering at 85° C.).

EXAMPLE 3
4-Chloro-N-[[4-methoxy-2-[3-(4-morpholinyl)-propoxy]phenyl]methyl]-N-(2-phenylethyl)benzamide, methanesulfonate salt (1:1)

A.
4-Methoxy-2-[3-(4-morpholinyl)propoxy]-benzaldehyde

2-Hydroxy-4-methoxybenzaldehyde (25 g) in 125 ml of dimethylformamide is treated first with 8.2 g of 50% sodium hydride, then with 36 g of N-(3-chloropropyl)-morpholine dissolved in 65 ml of toluene, following the procedure described in Example 1A, yielding 30.2 g of the title compound, boiling point 190°–195° C. at 0.1–0.2 mm of Hg.

B.
4-[3-[5-Methoxy-2-[[(2-phenylethyl)imino]methyl]-phenoxy]propyl]morpholine 4-Methoxy-2-[3-(4-morpholinyl)propoxy]-benzaldehyde (29.7 g) and 13.0 g of phenethylamine are reacted in 110 ml of toluene following the procedure described in Example 1B, yielding 33.1 g of the title compound, boiling point 240°–245° C. at 0.1–0.2 mm of Hg.

C.
4-[3-[5-Methoxy-2-[[(2-phenylethyl)-amino]methyl]-phenoxy]propyl]morpholine 4-[3-[5-Methoxy-2-[[(2-phenylethyl)imino]-methyl]-phenoxy]propyl]morpholine (33 g) is reduced with 9.8 g of sodium borohydride in 150 ml of methanol following the procedure described in Example 1C, yielding 25.8 g of the title compound, boiling point 249°–254° C. at 0.3–0.4 mm of Hg.

D.
4-Chloro-N-[[4-methoxy-2-[3-(4-morpholinyl)propoxy]phenyl]methyl]-N-(2-phenylethyl)benzamide, methanesulfonate salt (1:1)

4-[3-[5-Methoxy-2-[[(2-phenylethyl)amino]-methyl]-phenoxy]propyl]morpholine (12 g) and 5.8 g of p-chlorobenzoyl chloride are reacted in 160 ml of chloroform following the procedure described in Example 1D. The foamy residue from the chloroform evaporation (triturated with ether and evaporation repeated) is taken up in 75 ml of acetonitrile and diluted to 400 ml with ether. On seeding and rubbing, the crystalline hydrochloride salt separates. After cooling for 3 days, the product weighs 16.5 g, melting point 95°–98° C. (foaming; sintering at 80° C.).

EXAMPLE 4
4-Chloro-N-[[3-methoxy-2-[3-(4-morpholinyl)-propoxy]phenyl]methyl]-N-(2-phenylethyl)-benzamide, maleate salt (1:1)

A.
3-Methoxy-2-[3-(4-morpholinyl)-propoxy]benzaldehyde o-Vanillin (30.4 g), dissolved in 160 ml of dimethylformamide, is treated with 9.6 g of 50% sodium hydride, then with 130 ml of 2 N N-(3-chloropropyl)morpholine in toluene following the procedure described in Example 1A, yielding 42.9 g of the title compound, boiling point 178°–183° C. at 0.2–0.3 mm of Hg.

B.
N-[[3-Methoxy-2-[3-(4-morpholinyl)-propoxy]phenyl]methylene]benzeneethanamine 3-Methoxy-2-[3-(4-morpholinyl)propoxy]-benzaldehyde (42.5 g) and 18.5 g of phenethylamine are reacted in 150 ml of toluene following the procedure described in Example 1B, yielding 50.0 g of the title compound, boiling point 229°–234° C. at 0.2–0.3 mm of Hg.

C.
N-[[3-Methoxy-2-[3-(4-morpholinyl)-propoxy]phenyl]methyl]benzeneethanamine N-[[3-Methoxy-2-[3-(4-morpholinyl)propoxy]-phenyl]methylene]benzeneethanamine (49.7 g) is reduced with 14.8 g of sodium borohydride in 225 ml of methanol following the procedure described in Example 1C, yielding 40.2 g of the title compound, boiling point 0.2–0.3 mm of Hg.

D.
4-Chloro-N-[[3-methoxy-2-(4-morpholinyl)propoxy]-phenyl]methyl-N-(2-phenylethyl)benzamide, maleate salt (1:1)

N-[[3-Methoxy-2-[3-(4-morpholinyl)-propoxy]-phenyl]methyl]benzeneethanamine (20 g) and 9.6 g of p-chlorobenzoyl chloride are reacted in 250 ml of chloroform, following the procedure described in Example 1D. The syrupy residue from the chloroform evaporation cannot be crystallized and it is converted to the oily base using potassium carbonate and ether extractions. The base (25.2 g) and 5.6 g of maleic acid (the hydrochloride, hydrobromide, methanesulfonate, phosphate, citrate and succinate salts are oils or gums) are dissolved in 80 ml of warm acetonitrile and diluted to 480 ml with ether. On seeding and rubbing, the crystalline maleate salt separates. After cooling for 2 days, the product weighs 28.3 g, melting point 140°–142° C. Following recrystallization from 50 ml of acetonitrile, the product weighs 25.4 g, melting point 141°–143° C.

EXAMPLES 5–10

Following the procedure of Example 1, but substituting the compound listed in column I for 2-hydroxy-5-methoxybenzaldehyde, the compound listed in column II for N-(3-chloropropyl)-morpholine, the compound listed in column III for phenethylamine and the compound listed in column IV for p-chlorobenzoyl chloride, yields the compound listed in column V.

|    | Column I | Column II | Column III | Column IV | Column V |
|----|----------|-----------|------------|-----------|----------|
| 5. | 2-hydroxy-3-methoxy-benzaldehyde | N-(2-chloro-ethyl)pyrrolidine | n-propylamine | phenylacetyl chloride | N-[[3-methoxy-2-[2-(1-pyrrolidinyl)ethoxy]phenyl]-methyl]-N-(propyl)phenyl-acetamide |
| 6. | 2-hydroxy-4-ethoxy-benzaldehyde | N-(3-chloro-propyl)piperidine | cyclopropyl-amine | cinnamoyl chloride | N-(cyclopropyl)-N-[[4-ethoxy-2-[3-(1-piperidinyl)-propoxy]phenyl]methyl]-3-phenyl-2-propenamide |
| 7. | 2-hydroxy-5-methoxy-benzaldehyde | N-(4-chloro-butyl)piperazine | benzylamine | 3-(4-chloro-phenyl)-2-propenoyl chloride | N-benzyl-3-(4-chlorophenyl)-N-[[5-methoxy-2-[4-(1-piperazinyl)butoxy]phenyl]-methyl]-2-propenamide |
| 8. | 2-hydroxy-3-butoxy benzaldehyde | 4-methyl-1-(5-chloropentyl)-piperazine | isopropylamine | cyclohexanoyl chloride | N-(isopropyl)-N-[[3-butoxy-2-[5-(4-methyl-1-piperazinyl)-pentoxy]phenyl]methyl]cyclo-hexanamide |
| 9. | 2-hydroxy-4-methoxy-benzaldehyde | N-(2-chloro-ethyl)morpholine | phenethylamine | benzenesulfonyl chloride | N-[[4-methoxy-2-[2-(4-morpholinyl) ethoxy]phenyl]-methyl]-N-(phenylethyl)-benzenesulfonamide |
| 10. | 2-hydroxy-6-methoxy-benzaldehyde | 3-dimethylamino-propyl chloride | 4-methoxy-aniline | 3-(trifluoromethyl)-benzoyl chloride | N-[[2-[3-dimethylamino)-propoxy]-6-methoxyphenyl-methyl]-N-(4-methoxy- |

| Column I | Column II | Column III | Column IV | Column V |
| --- | --- | --- | --- | --- |
| | | | | phenyl)-3-(trifluoromethyl)benzamide |

What is claimed is:

1. A compound having the formula

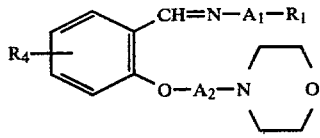

wherein $R_1$ is alkyl, cycloalkyl or aryl; $R_4$ is alkoxy; $A_1$ is a saturated bond or an alkylene group having 1 to 4 carbon atoms; and $A_2$ is an alkylene group having 2 to 5 carbon atoms; wherein alkyl and alkoxy are groups having 1 to 6 carbon atoms; cycloalkyl is a group having 3 to 7 carbon atoms; and aryl is phenyl or phenyl substituted with a halogen, alkyl, alkoxy, trifluoromethyl, nitro or amino group.

2. The compound in accordance with claim 1 having the name 4-[3-[4-methoxy-2-[[(2-phenylethyl)imino]methyl]-phenoxy]propyl]morpholine.

3. The compound in accordance with claim 1 having the name 4-[3-[5-methoxy-2-[[(2-phenylethyl)imino]methyl]phenoxy]propyl]morpholine.

4. The compound in accordance with claim 1 having the name N-[[3-methoxy-2-[3-(4-morpholinyl)propoxy]phenyl]methylene]benzeneethanamine.

* * * * *